US011467159B2

(12) United States Patent
Weichert et al.

(10) Patent No.: US 11,467,159 B2
(45) Date of Patent: Oct. 11, 2022

(54) LUMINESCENT PHOSPHOLIPID ANALOGS FOR THE IDENTIFICATION AND ISOLATION OF CIRCULATING TUMOR CELLS

(71) Applicant: CELLECTAR BIOSCIENCES, INC., Madison, WI (US)

(72) Inventors: Jamey P. Weichert, Madison, WI (US); Chorom Pak, Madison, WI (US); Anatoly Pinchuk, Madison, WI (US); Kevin Kozak, Madison, WI (US); Marc Longino, Madison, WI (US)

(73) Assignee: CELLECTAR BIOSCIENCES, INC., Madison, WI (US)

( * ) Notice: Subject to any disclaimer, the term of this patent is extended or adjusted under 35 U.S.C. 154(b) by 522 days.

(21) Appl. No.: 15/623,309

(22) Filed: Jun. 14, 2017

(65) Prior Publication Data

US 2017/0356914 A1 Dec. 14, 2017

Related U.S. Application Data

(60) Provisional application No. 62/349,713, filed on Jun. 14, 2016.

(51) Int. Cl.
*G01N 33/574* (2006.01)
*G01N 21/64* (2006.01)
(Continued)

(52) U.S. Cl.
CPC .......... *G01N 33/574* (2013.01); *G01N 15/14* (2013.01); *G01N 33/54326* (2013.01);
(Continued)

(58) Field of Classification Search
CPC .......... G01N 15/14; G01N 2015/1006; G01N 2015/1488; G01N 21/6428; G01N 2021/6439
See application file for complete search history.

(56) References Cited

U.S. PATENT DOCUMENTS 6,365,362 B1 4/2002 Terstappen et al.
7,811,548 B1 10/2010 Pinchuk et al.
(Continued)

FOREIGN PATENT DOCUMENTS

JP 2008545614 A 12/2008
JP 2012526822 A 11/2012
(Continued)

OTHER PUBLICATIONS

Dean, John M. et al. "Review: Structural and functional roles of ether lipids," Protein Cell 2018, 9(2):196-206 (Year: 2018).*
(Continued)

*Primary Examiner* — Jennifer Wecker
*Assistant Examiner* — Michelle Adams
(74) *Attorney, Agent, or Firm* — Michael Best & Friedrich LLP

(57) ABSTRACT

The present invention is directed to a method of identifying, isolating, and enabling downstream analysis of circulating tumor cells comprising contacting a blood or blood serum sample of a subject with a composition comprising a phospholipid ether analog bound to a luminescent molecule or a magnetic bead and subjecting the blood or blood serum sample of the subject to fluorescent microscopy, flow cytometry or magnetic isolation.

8 Claims, 1 Drawing Sheet

A

B

(51) Int. Cl.
  G01N 15/14    (2006.01)
  G01N 33/58    (2006.01)
  G01N 33/543   (2006.01)
  G01N 15/00    (2006.01)
  G01N 15/10    (2006.01)

(52) U.S. Cl.
  CPC ..... *G01N 33/57492* (2013.01); *G01N 33/582* (2013.01); *G01N 21/6428* (2013.01); *G01N 2015/0065* (2013.01); *G01N 2015/1006* (2013.01); *G01N 2021/6439* (2013.01)

(56) References Cited

U.S. PATENT DOCUMENTS

| | | | |
|---|---|---|---|
| 9,925,283 B2* | 3/2018 | Weichert | A61K 51/0489 |
| 2007/0020178 A1 | 1/2007 | Weichart et al. | |
| 2009/0047656 A1 | 2/2009 | Baden et al. | |
| 2010/0286510 A1* | 11/2010 | Pinchuk | A61B 5/0071 600/431 |
| 2012/0178645 A1 | 7/2012 | Foekens et al. | |

FOREIGN PATENT DOCUMENTS

| | | |
|---|---|---|
| JP | 2016512197 A | 4/2016 |
| WO | 2016013041 A1 | 1/2016 |

OTHER PUBLICATIONS

Chen, J.-Y. et al. "Sensitive and Specific Biomimetic Lipid Coated Microfluidics to Isolate Viable Circulating Tumor Cells and Microemboli for Cancer Detection," PLoS ONE 11(3): e0149633. https://doi.org/10.1371/journal.pone.0149633. Published Mar. 3, 2016. (Year: 2016).*
Martina, M.-S. et al. "Magnetic Targeting of Rhodamine-Labeled Superparamagnetic Liposomes to Solid Tumors: In Vivo Tracking by Fibered Confocal Fluorescence Microscopy," Molecular Imaging, vol. 6, No. 2 (Mar.-Apr. 2007): pp. 140-146 (Year: 2007).*
Quesada, E. et al. "Fluorescent Phenylpolyene Analogues of the Ether Phospholipid Edelfosine for the Selective Labeling of Cancer Cells," Journal of Medicinal Chemistry, 2004, vol. 47, No. 22, 5333-5335. (Year: 2004).*
Wen, C.-Y. "Quick-Response Magnetic Nanospheres for Rapid, Efficient Capture and Sensitive Detection of Circulating Tumor Cells," ACS Nano 2014, 8, 1, 941-949 (Year: 2014).*
He, W. et al. "Quantitation of circulating tumor cells in blood samples from ovarian and prostate cancer patients using tumor-specific fluorescent ligands," Int. J. Cancer: 123, 1968-1973 (2008) (Year: 2008).*
Eurasian Patent Office Action for Application No. 201892663 dated Dec. 7, 2019 (5 pages, English translation included).
Constantin et al., "Fluorescent porphyrin with an increased uptake in peripheral blood cell subpopulations from colon cancer patients," Med Chem, 2015, 11(4):354-63, Abstract.
European Patent Office Extended Search Report for Application No. 17814042.2 dated Jan. 20, 2020 (7 pages).
Alix-Panabieres et al., "Challenges in circulating tumour cell research," Nature Reviews Cancer, 2014, 14(9):623-631.
Cohen et al., "Relationship of circulating tumor cells to tumor response, progression-free survival, and overall survival in patients with metastatic colorectal cancer," Journal of Clinical Oncology, 2008, 26(19):3213-3221.
Cristofanilli et al., "Circulating tumor cells, disease progression, and survival in metastatic breast cancer," The New England Journal of Medicine, Aug. 19, 2004, 351(8), 781-791.
Eichelberg et al., "Epithelial cell adhesion molecule is an independent prognostic marker in clear cell renal carcinoma," International Journal of Cancer, 2013, 132(12):2948-2955.
Faltas, "Cornering metastases: therapeutic targeting of circulating tumor cells and stem cells," Frontiers in Oncology, 2012, (2)68:1-7.

Hayes et al., Circulating tumor cells at each follow-up time point during therapy of metastatic breast cancer patients predict progression-free and overall survival, Clinical Cancer Research, 2006, 12(14):4218-4224.
Himo et al., "Copper(I)-catalyzed synthesis of azoles. DFT study predicts unprecedented reactivity and intermediates," Journal of the American Chemical Society, 2005, 127(1):210-216.
Ignatiadas et al., "Circulating tumor cells and circulating tumor DNA for precision medicine: dream or reality?," Annals of Oncology, 2014, 25(12): 2304-2313.
International Search Report and Written Opinion for Application No. PCT/US2017/37549 dated Sep. 5, 2017 (7 pages).
Paiva et al., "Detailed characterization of multiple myeloma circulating tumor cells shows unique phenotypic, cytogenetic, functional, and circadian distribution profile," Blood, 2013,122(22):3591-3598.
Roberts et al., "Kappa agonist CovX-Bodies," Bioorganic and Medicinal Chemistry Letters, 2012, 22(12):4173-4178.
Sato et al., "Chemically Programmed Antibodies as HIV-1 Attachment Inhibitors," ACS Medicinal Chemistry Letters, 2013,4(5):460-465.
Scatena et al., "Circulating tumour cells and cancer stem cells: a role for proteomics in defining the interrelationships between function, phenotype and differentiation with potential clinical applications," Biochimica Biophysica Acta, 2013, 1835(2):129-143.
Spizzo et al., "EpCAM expression in primary tumour tissues and metastases: an immunohistochemical analysis," Journal of Clinical Pathology, 2011, 64(5):415-420.
Toss et al., "CTC enumeration and characterization: moving toward personalized medicine," Annals of Translational Medicine, 2014, 2(11):108.
Weichert et al., "Alkylphosphocholine analogs for broad-spectrum cancer imaging and therapy," Science Translational Medicine, 2014, 6(240):240ra75.
Yap et al., "Circulating tumor cells: a multifunctional biomarker," Clinical Cancer Research, 2014, 20(10):2553-2568.
Yu et al., "Circulating breast tumor cells exhibit dynamic changes in epithelial and mesenchymal composition," Science, 2013, 339(6119):580-584.
Eurasian Patent Office Action for Application No. 201892663 dated Jun. 16, 2020 (5 pages, English translation included).
Eurasian Patent Office Action for Application No. 201892663 dated Feb. 26, 2021 (4 pages including English translation).
Intellectual Property Office of India Examination Report for Application No. 201817047209 dated Mar. 17, 2021 (6 pages including English translation).
Japanese Patent Office Notice of Reasons for Rejection for Application No. 2019518376 dated Jun. 8, 2021 (11 pages including English translation).
Saudi Authority for Intellectual Property First Examination Report for Application No. 518400643 dated Jun. 30, 2021 (8 pages including statement of relevance).
Canadian Patent Office Action for Application No. 3,027,497 dated Aug. 18, 2021 (4 pages).
Korean Patent Office Notification of Reason for Refusal for Application No. 10-2019-7000619 dated Aug. 24, 2021 (12 pages including English translation).
National Intellectual Property Administration People's Republic of China First Office Action for Application No. 2017800485432 dated Sep. 17, 2021 (18 pages including English translation).
Japanese Patent Office Notice of Reasons for Rejection for Application No. 2019-518376 dated Nov. 30, 2021 (10 pages including English translation).
State of Israel Patent Office action for Application No. 263687 dated Jan. 12, 2022 (6 pages including English translation).
National Intellectual Property Administration P.R. China Second Office Action for Application No. 2017800485432 dated Apr. 29, 2022 (19 pages including English translation).
Korean Patent Office Notice of Final Rejection for Application No. 10-2019-7000619 dated Mar. 29, 2022 (7 pages including English translation).

(56) References Cited

OTHER PUBLICATIONS

New Zealand Patent Office action for Application No. 749272, dated Jul. 14, 2022 (4 pages).

* cited by examiner

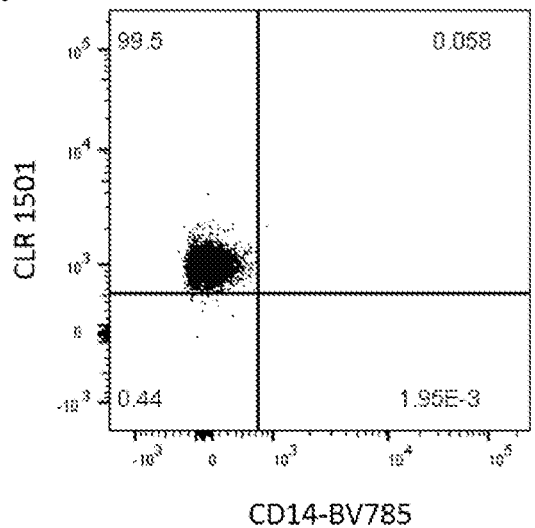 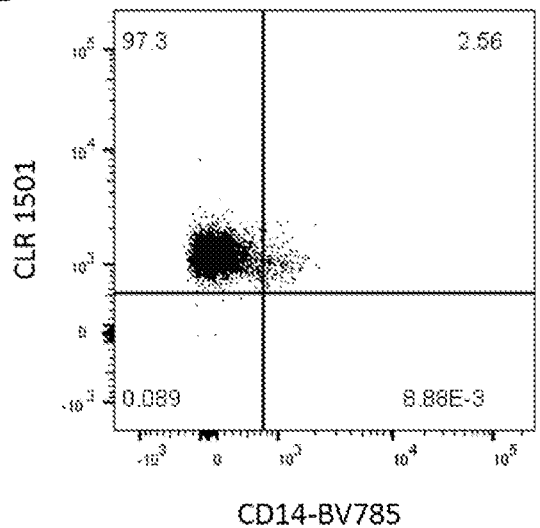

LUMINESCENT PHOSPHOLIPID ANALOGS FOR THE IDENTIFICATION AND ISOLATION OF CIRCULATING TUMOR CELLS

CROSS-REFERENCE TO RELATED APPLICATION(S)

This application claims priority to U.S. Provisional Patent Application No. 62/349,713, filed on Jun. 14, 2016, the entire contents of which are fully incorporated herein by reference.

BACKGROUND

Circulating tumor cells ("CTCs") are a blood-based marker hypothesized to have predictive and prognostic value in cancer detection and progression. Specifically, CTCs are theorized to be a minimally invasive source of tumor cells from both the primary tumor and metastatic sites. (Alix-Panabieres C, et al., Challenges in circulating tumour cell research, *Nat Rev Cancer,* 2014 September, 14(9), 623-31 and Yap T, et al., Circulating tumor cells: a multifunctional biomarker, *Clin Cancer Res,* 2014 May 15, 20(10), 2553-68.) Many cancer types are known or predicted to give rise to CTCs, including multiple myeloma. Paiva B, et al., Detailed characterization of multiple myeloma circulating tumor cells shows unique phenotypic, cytogenetic, functional, and circadian distribution profile, *Blood,* 2013 Nov. 21, 122(22), 3591-3598. Further, cancer stem cells ("CSC") another possible cancer cell type predicted to have prognostic value are theorized to be a subpopulation of CTCs. Scatena R et al., Circulating tumour cells and cancer stem cells: a role for proteomics in defining the interrelationships between function, phenotype and differentiation with potential clinical applications, Biochim Biophys Acta, 2013 April; 1835(2), 129-143; Faltas B. Cornering metastases: therapeutic targeting of circulating tumor cells and stem cells, *Front Oncol,* 2012 Jul. 3, (2) 68. By definition, a CTC is a nucleated, CD45 negative, epithelial cell adhesion molecule ("EpCAM") positive, and pan-cytokeratin positive cell. However, identification and isolation of CTCs from whole blood is technically challenging because CTCs are extremely rare and can be as low as 1 cell in 7.5 milliliters ("mL") of blood (i.e. 1 in several billion cells).

Currently, the only accepted and approved indication for CTCs is enumeration as a prognostic marker of cancer progression. The CellSearch® System (CellSearch is a registered trademark of Johnson & Johnson Corp) is currently the only assay that is FDA-approved to enumerate CTCs. (Ignatiadas M, et al., Circulating tumor cells and circulating tumor DNA for precision medicine: dream or reality?, *Ann Oncol,* 2014 December, 25(12), 2304-13 and Toss A, et al., CTC enumeration and characterization: moving toward personalized medicine, *Ann Transl Med,* 2014 November, 2(11):108, 1-16.) Unfortunately, CellSearch® is only approved for metastatic breast, colorectal, and prostate cancer. (Hayes D F, et al., Circulating tumor cells at each follow-up time point during therapy of metastatic breast cancer patients predict progression-free and overall survival, *Clin Cancer Res,* 2006 Jul. 15, 12(1), 4218-24; Cristofanilli M, et al., Circulating tumor cells, disease progression, and survival in metastatic breast cancer, *N Engl J Med,* 2004 Aug. 19, 351(8), 781-91; De Bono J S, et al., Circulating tumor cells predict survival benefit from treatment in metastatic castration-resistant prostate cancer, *Clin Cancer Res,* 2008 Oct. 1, 14(19), 6302-9; and Cohen S J, et al., Relationship of circulating tumor cells to tumor response, progression-free survival, and overall survival in patients with metastatic colorectal cancer, *J Clin Oncol,* 2008 Jul. 1, 26(19), 3213-21.)

There remain challenges to identifying CTCs under the current definition. First, there is potential for false-positive findings due to EpCAM-positive circulating epithelial cells. Second, false-negative findings may occur due to tumor cells undergoing an epithelial-to-mesenchymal transition resulting in reduced expression of epithelial markers. (Yu M, et al., Circulating breast tumor cells exhibit dynamic changes in epithelial and mesenchymal composition, *Science,* 2013 Feb. 1, 339(6119), 580-4.) Third, there is growing evidence in literature that not all CTCs express EpCAM and that certain cancer types, such as renal cancer, have low or heterogeneous expression of EpCAM. (Eichelberg C, et al., Epithelial cell adhesion molecule is an independent prognostic marker in clear cell renal carcinoma, *Int J Cancer,* 2013 Jun. 15, 132(12), 2948-55 and Spizzo G, et al., EpCAM expression in primary tumour tissues and metastases: an immunohistochemical analysis, *J Clin Pathol,* 2011 May, 64(5):415-20.) Thus, there is a clinical need for an economic and robust assay using a broad tumor marker that can identify potentially all CTCs without bias. Cancer-targeted alkylphosphocholine ("APC") analogs offer a novel method for the identification and isolation of CTCs from a broad range of different cancer types.

SUMMARY OF THE INVENTION

The present invention is directed to a method of identifying one or more circulating tumor cells comprising:
(i) contacting a blood or blood serum sample from a subject with a composition comprising a phospholipid ether ("PLE") analog bound to an article selected from the group consisting of a luminescent molecule and a magnetic bead; and
(ii) subjecting the blood or blood serum sample from the subject to fluorescent microscopy or flow cytometry,
wherein if the article is a magnetic bead the article is bound to the PLE via a linker.

The present invention is further directed to a method of isolating one or more circulating tumor cells comprising the steps of:
(i) administering to a subject a composition comprising a PLE analog bound to an article selected from the group consisting of a luminescent molecule and a magnetic bead; and
(ii) subjecting the blood or blood serum sample from the subject to flow cytometry or a magnetic field,
wherein if the article is a magnetic bead the article is bound to the PLE via a linker and the blood or blood serum sample from the subject is subjected to a magnetic field and wherein if the article is a luminescent molecule then the blood or blood serum sample from the subject is subjected to flow cytometry.

In one embodiment, the one ore more circulating tumor cells comprise cancer stem cells.

In a preferred embodiment, the PLE analog bound to an article, of the present invention is a compound selected from the group consisting of formula (I), formula (II)

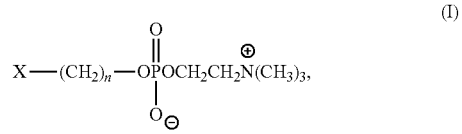

formula (III)

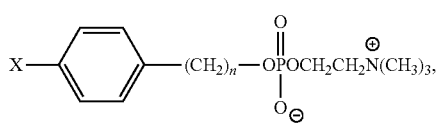
(II)

formula (IV)

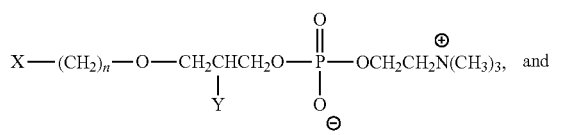
(III)

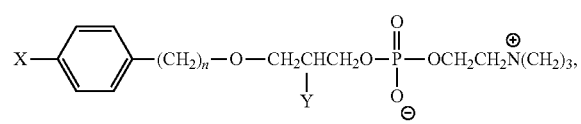
(IV)

wherein:

n is an integer from 16 to 30, preferably 18;

Y is selected from the group consisting of —H, —OH, —OR$^1$, —C(O)OH, and —OC(O)R$^1$, wherein R$^1$ is an alkyl; and X is a luminescent molecule or a magnetic bead.

In a preferred embodiment the luminescent molecule is a fluorophore, more preferably the fluorophore is selected from the group consisting of

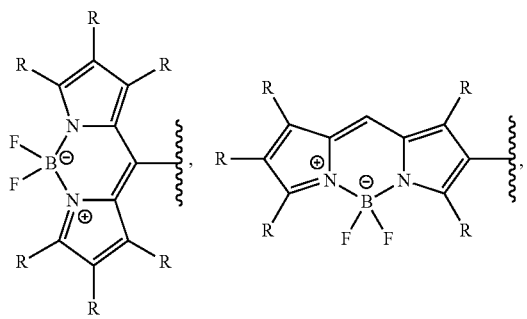

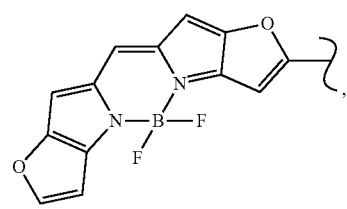

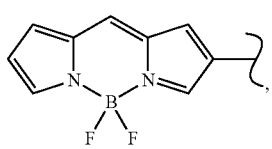

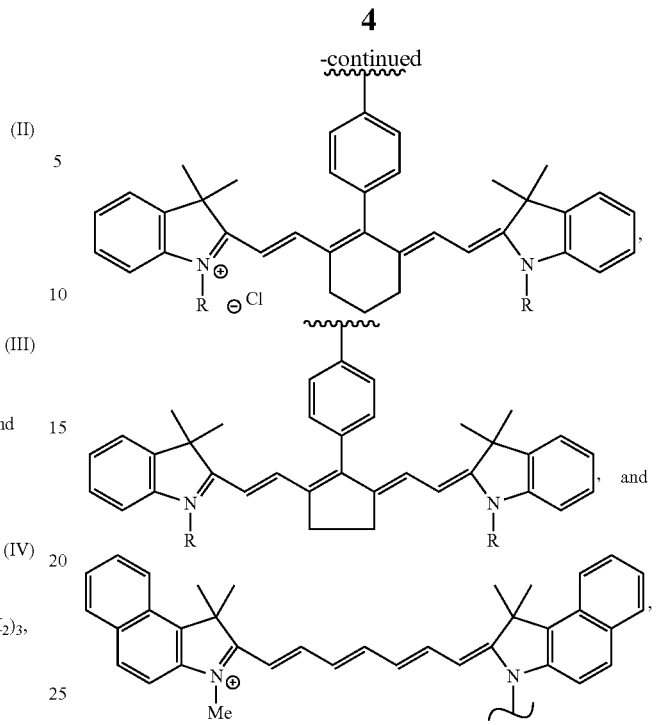

wherein each R is independently selected from H, CH$_3$, C$_2$H$_5$ and C$_3$H$_7$, most preferably

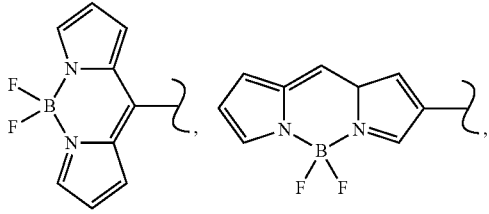

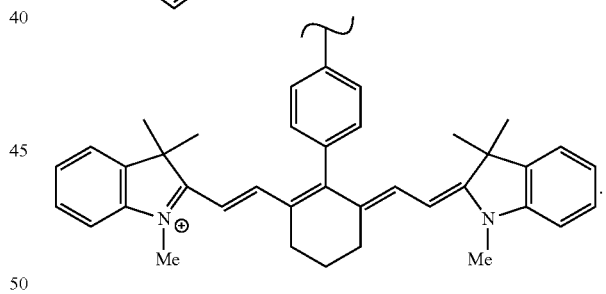

In another preferred embodiment the magnetic bead is selected from the group consisting of nano-magnetic beads, micro-magnetic beads, paramagnetic beads and super paramagnetic beads, wherein the magnetic bead is bound to the PLE analog via a linker selected from the group consisting of a biotin-streptavidin linker, an azetidinone linker, and an amine-, azide-, alkyne-, carboxyl- and hydroxyl group linker and combinations thereof.

In another preferred embodiment, the one or more circulating tumor cells of the present invention are selected from the group consisting of a breast cancer, a lung cancer, a thyroid cancer, a cervical cancer, a squamous cell carcinoma, a prostate cancer, a pancreas cancer, and a colorectal cancer cell, a multiple myeloma cell, a cancer stem cell, preferably a breast cancer, a lung cancer, a thyroid cancer, a cervical cancer, a squamous cell carcinoma, a prostate cancer, a pancreas cancer and a colorectal cancer cell, and more preferably a prostate cancer cell or a pancreas cancer cell.

In another preferred embodiment, the methods of the present invention may be utilized in further downstream data acquisition technologies including, but not limited to, protein isolation, RNA isolation, DNA isolation, gene translocation and/or amplification analysis and fluorescent in-situ hybridization.

BRIEF DESCRIPTION OF THE DRAWINGS

FIG. 1. Plot analysis of CD45−, CD34− cells isolated from patient 108 (colorectal cancer.) Panel A shows cells stained with for all markers except CD14. Panel B shows cells stained with all markers. Upper left quadrant indicates CD14−/CLR1501+ cells, upper right indicates CD14+/CLR1501+, bottom right indicates CD14+/CLR1501−, and bottom left indicates CD14−/CLR1501.

DETAILED DESCRIPTION OF THE INVENTION

PLE analogs have the ability to identify, isolate, and enable downstream analysis of CTCs of all types. Cancer cells have five to ten times more lipid rafts than healthy cells. Lipid rafts are specialized regions of the membrane phospholipid bilayer that contain high concentrations of cholesterol and sphingolipids and serve to organize cell surface and intracellular signaling molecules (e.g., growth factor and cytokine receptors, the phosphatidylinositol 3-kinase (PI3K)/Akt survival pathway). Data suggests that lipid rafts serve as portals of entry for PLEs. The marked selectivity of these compounds for cancer cells versus non-cancer cells is attributed to the high affinity of PLEs for cholesterol and the abundance of cholesterol-rich lipid rafts in cancer cells. The pivotal role played by lipid rafts is underscored by the fact that disruption of lipid raft architecture suppresses uptake of PLEs into cancer cells. It has been shown that the uptake of PLEs is reduced by 60% when lipid rafts are blocked from forming.

Preliminary results obtained in over 55 xenograft and spontaneous tumor models have universally shown CLR1404 to undergo selective uptake and prolonged retention in tumors. Weichert, J P et al., Alkylphosphocholine analogs for broad-spectrum cancer imaging and therapy, Sci Transl Med, 2014, Jun. 11, 6(240ra75). What was not known previously was whether PLE analogs were capable of being taken up by CTCs to the extent that the CTCs could be identified and isolated.

The present invention is directed to a method of identifying one or more circulating tumor cells comprising:
(i) contacting a blood or blood serum sample from a subject with a composition comprising a phospholipid ether ("PLE") analog bound to an article selected from the group consisting of a luminescent molecule and a magnetic bead; and
(ii) subjecting the blood or blood serum sample from the subject to fluorescent microscopy or flow cytometry, wherein if the article is a magnetic bead the article is bound to the PLE via a linker.

The present invention is further directed to a method of isolating one or more circulating tumor cells comprising the steps of:
(i) contacting a blood or blood serum sample from a subject with a composition comprising a PLE analog bound to an article selected from the group consisting of a luminescent molecule and a magnetic bead; and
(ii) subjecting a blood or blood serum sample from the subject to flow cytometry, preferably fluorescence activated cell sorting or a magnetic field, wherein if the article is a magnetic bead the article is bound to the PLE via a linker and the blood or blood serum sample from the subject is subjected to a magnetic field and wherein if the PLE analog is bound to a luminescent molecule then the blood or blood serum sample from the subject is subjected to flow cytometry.

In a preferred embodiment, the PLE analog bound to an article, of the present invention is a compound selected from the group consisting of formula (I), formula (II)

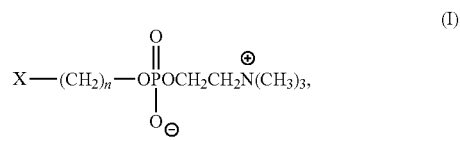

formula (III)

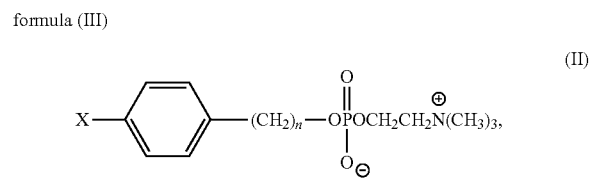

formula (IV)

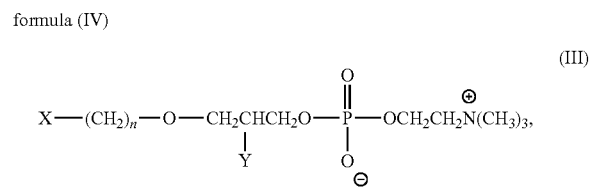

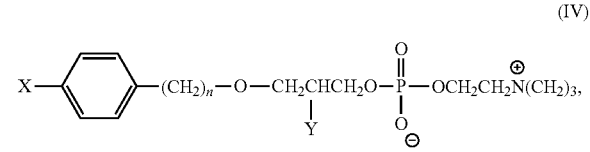

wherein:
n is an integer from 16 to 30, preferably 18;
Y is selected from the group consisting of —H, —OH, —OR$^1$, —C(O)OH, and —OC(O)R$^1$, wherein
R$^1$ is an alkyl; and
X is a luminescent molecule or a magnetic bead.

In a preferred embodiment the luminescent molecule is a fluorophore, more preferably the fluorophore is selected from the group consisting of

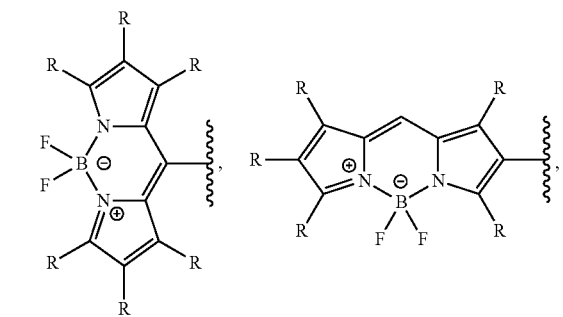

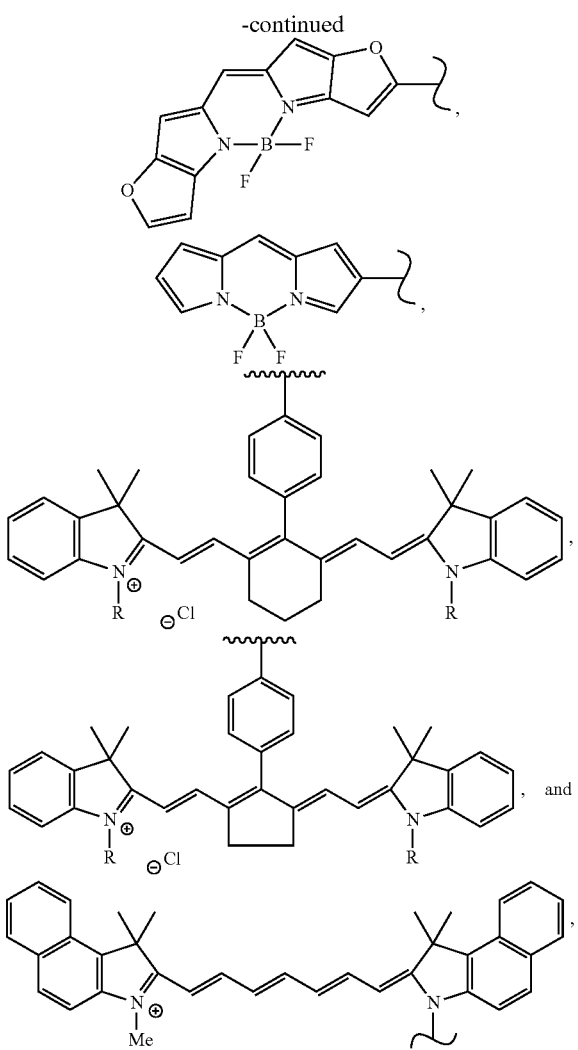

wherein each R is independently selected from H, CH₃, C₂H₅ and C₃H₇, most preferably

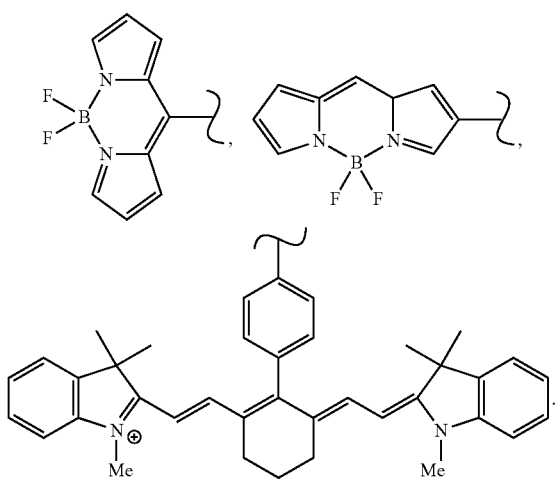

In another preferred embodiment the magnetic bead is selected from the group consisting of nano-magnetic beads, micro-magnetic beads, paramagnetic beads and super paramagnetic beads, wherein the magnetic bead is bound to the PLE analog via a linker selected from the group consisting of a biotin-streptavidin linker, an azetidinone linker, and an amine-, azide-, alkyne-, carboxyl- and hydroxyl group linker and combinations thereof.

In another preferred embodiment, the one or more circulating tumor cells of the present invention are selected from the group consisting of a breast cancer, a lung cancer, a thyroid cancer, a cervical cancer, a squamous cell carcinoma, a prostate cancer, a pancreas cancer and a colorectal cancer cell and a cancer stem cell and a malignant plasma cell, preferably a prostate cancer cell or a pancreas cancer cell.

In another preferred embodiment, the methods of the present invention may be utilized in further downstream data acquisition technologies including, but not limited to, protein isolation, RNA isolation, DNA isolation, gene translocation and/or amplification analysis and fluorescent in-situ hybridization.

Definitions

In general, reference to "a circulating tumor cell" is intended to refer to a single cell, while reference to "circulating tumor cells" or "cluster of circulating tumor cells" is intended to refer to more than one cancer cell. However, one of skill in the art would understand that reference to "circulating tumor cells" is intended to include a population of circulating tumor cells including one or more circulating tumor cells while reference to "a circulating tumor cell" could include more than one circulating tumor cell.

The term "circulating tumor cell" or "circulating tumor cells", as used herein, refers to any cancer cell or cluster of cancer cells that are found in a subject's blood or blood serum sample. CTCs may also contain or consist of a cancer stem cell or cluster of cancer stem cells that are found in a subject's blood or blood serum sample.

As used herein the term "cancer stem cell" refers to a cancer cell capable of self-renewing and differentiating into the distinct types of cancer cells found in a malignant tumor.

The term "cancer", as used herein, refers to, but is not limited to, a variety of cancer types including breast cancer including male breast cancer; digestive/gastrointestinal cancers including anal cancer, appendix cancer, extrahepatic bile duct cancer, gastrointestinal carcinoid tumor, colon cancer, esophageal cancer, gallbladder cancer, gastric cancer, gastrointestinal stromal tumors ("gist"), Islet cell tumors, adult primary liver cancer, childhood liver cancer, pancreatic cancer, rectal cancer, small intestine cancer, and stomach (gastric) cancer; endocrine and neuroendocrine cancers including pancreatic adenocarcinoma, adrenocortical carcinoma, pancreatic neuroendocrine tumors, Merkel cell carcinoma, non-small cell lung neuroendocrine tumor, small cell lung neuroendocrine tumor, parathyroid cancer, pheochromocytoma, pituitary tumor and thyroid cancer; eye cancers including intraocular melanoma and retinoblastoma; genitourinary cancer including bladder cancer, kidney (renal cell) cancer, penile cancer, prostate cancer, transitional cell renal pelvis and ureter cancer, testicular cancer, urethral cancer and Wilms tumor; germ cell cancers including childhood central nervous system cancer, childhood extracranial germ cell tumor, extragonadal germ cell tumor, ovarian germ cell tumor and testicular cancer; gynecologic cancers including cervical cancer, endometrial cancer, gestational trophoblastic tumor, ovarian epithelial cancer, ovarian germ cell tumor, uterine sarcoma, vaginal cancer and vulvar cancer; head and neck cancers including hypopharyngeal cancer, laryngeal cancer, lip and oral cavity cancer, metastatic squamous neck cancer with occult primary, mouth cancer, nasopharyngeal cancer, oropharyngeal cancer, paranasal sinus and nasal cavity cancer, parathyroid cancer, pharyngeal cancer, salivary gland cancer and throat cancer; leukemias including adult acute lymphoblastic leukemia, childhood acute lymphoblastic leukemia, adult acute myeloid leukemia, childhood acute myeloid leukemia, chronic lymphocytic leukemia, chronic myelogenous leukemia and hairy cell leukemia; multiple myeloma including malignant plasma cells; lymphomas including AIDS-related lymphoma, cutaneous t-cell lymphoma, adult Hodgkin lymphoma, childhood Hodgkin lymphoma, Hodgkin lymphoma during pregnancy, mycosis fungoides, adult non-Hodgkin lymphoma, childhood non-Hodgkin lymphoma, non-Hodgkin lymphoma during pregnancy, primary central nervous system lymphoma, Sézary syndrome and Waldenström macroglobulinemia; musculoskeletal cancers including Ewing sarcoma, osteosarcoma and malignant fibrous histocytoma of bone, childhood rhabdomyosarcoma and soft-tissue sarcoma; neurological cancers including adult brain tumor, childhood brain tumor, astrocytomas, brain stem glioma, central nervous system atypical teratoid/rhabdoid tumor, central nervous system embryonal tumors, craniopharyngioma, ependymoma, neuroblastoma, primary central nervous system (CNS) lymphoma; respiratory/thoracic cancers including non-small cell lung cancer, small cell lung cancer, malignant mesothelioma, thymoma and thymic carcinoma; and skin cancers including Kaposi sarcoma, melanoma and squamous cell carcinoma.

As used herein, the term "sample" refers to any sample suitable for the methods provided by the present invention. The sample may be any sample that includes circulating tumor cells suitable for detection. Sources of samples include whole blood, bone marrow, pleural fluid, peritoneal fluid, central spinal fluid, urine, saliva and bronchial washes. In one aspect, the sample is a blood sample, including, for example, whole blood or any fraction or component thereof. A blood sample, suitable for use with the present invention may be extracted from any source known that includes blood cells or components thereof, such as veinous, arterial, peripheral, tissue, umbilical cord, and the like. For example, a sample may be obtained and processed using well known and routine clinical methods (e.g., procedures for drawing and processing whole blood). In an embodiment, an exemplary sample may be peripheral blood drawn from a subject with cancer.

As used herein the term "identify" or "identifying" refers to visualizing the existence of a CTC.

As used herein the term "isolate" or "isolating" refers to physically separating CTCs from other cell types found in a subject's sample.

As used herein the term "contact" or "contacting" refers to bringing a subject, tissue, organ or cells in contact with a PLE analog of the present invention. As used herein, contact can be accomplished ex vivo or in vitro, i.e. in a test tube, in cells or tissues of living organisms, for example, humans. A "patient" or "subject", used equivalently herein, refers to a mammal, preferably a human.

As used herein the term "alkyl" refers to a branched or straight-chain alkyl consisting of a saturated hydrocarbon group of 1 to 24 carbon atoms ($C_1$-$C_{24}$) unless otherwise stated. The alkyl group can be cyclic or acyclic.

As used herein the term "amine" refers to a functional group that contains a nitrogen atom with a lone pair of electrons.

As used herein the term "azide" refers to a functional group that contains three consecutive nitrogen atoms.

As used herein the term "alkyne" refers to a functional group that contains two carbon atoms that are triple bonded to each other.

As used herein the term "carboxyl" refers to a functional group that contains a C(O)O structure.

As used herein the term "hydroxyl" refers to a functional group that contains an OH.

As used herein "n" is an integer from 16 to 30.

As used herein "Y" is selected from the group consisting of —H, —OH, —OR, —C(O)OH, and —OC(O)R.

As used herein "R" refers to an alkyl.

As used herein the term "R" refers to an H, $CH_3$, $C_2H_5$ and $C_3H_7$.

As used herein "X" is a luminescent molecule or a magnetic bead bound to a linker.

Flow cytometry useful in the present invention includes, but is not limited to, fluorescence activated cell sorting ("FACS") and multi-color flow cytometry.

Magnetic beads useful in the present invention include, but are not limited to, nano-magnetic beads having a size in the nanometer range and are sometimes referred to as magnetic nanoparticles, for example 50 nM MACS® beads, (MACS is a registered trademark of and available from Miltenyi Biotec GmbH), micro-magnetic beads having a size in the micrometer range, for example 1-3 µM Dynabeads® (Dynabeads is a registered trademark of and available from Invitrogen Dynal AS Corp), paramagnetic beads and super paramagnetic beads.

Luminescent molecules useful in the present invention include fluorophores.

Fluorophores include, but are not limited to, Alexa Fluor® (Alex Fluor is a registered trademark of and available from Molecular Probes, Inc.) compounds including 350, 405, 430, 488, 532, 546, 555, 568, 594, 610, 633, 635, 647, 660, 680, 700, 750 and 790, Brilliant Violet™ (Brilliant Violet is available from BioLegend®) compounds including 420, 510, 605, 650, 711 and 786, Brilliant Ultra-Violet™ (Brilliant Ultra-Violet is available from BD Biosciences, Inc.) compounds including those of the following frequency 395 and 737 nm, Dylight® (Dylight is a registered trademark of and available from Pierce Biotechnology, Inc.) compounds including 350, 405, 488, 550, 594, 633, 650, 680, 755 and 800, Violetfluor® 450, Redfluor® 710, (Violetfluor and Redfluor are a registered trademark of and available from Tonbo Biotechnologies Corporation), allophycocyanin ("APC"), APC Alexa Fluor® 750, APC-Cy7, peridinin-chlorophyll proteins ("PerCP"), PerCP-Cy5, PerCP-Cy5.5, PerCP-Cy7, propidium iodide ("PI"), phycoerythrin ("PE"), PE-Cy5, PE-Cy5.5, PE-Cy7, PE-Texas Red® (Texas Red is a registered trademark of Molecular Probes, Inc.), fluorescein ("FITC"), aminimeteylcourmarin ("AMCA"), Marina Blue®, Cascade Blue® (Marina Blue and Cascade Blue are registered trademark and available from Molecular Probes, Inc.), Cascade Yellow, Pacific Blue, Qdot® 605 (Qdot is a registered trademark of Life Technologies Corp), tetramethylrhodamine ("TR1TC"), Cy3, Cy5, Cy5.5, Texas Red® and compounds of the following structures,

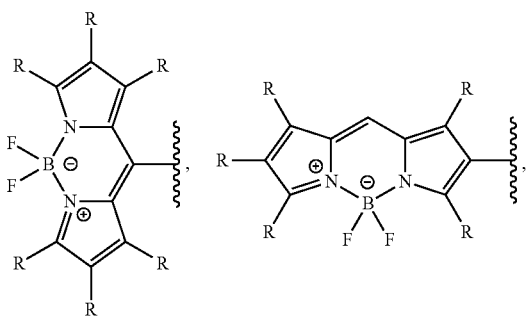

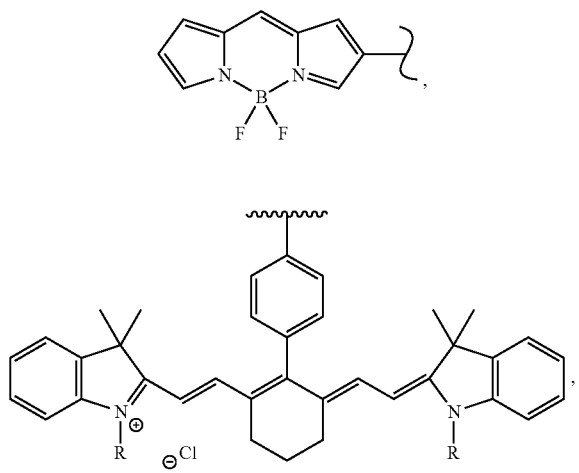

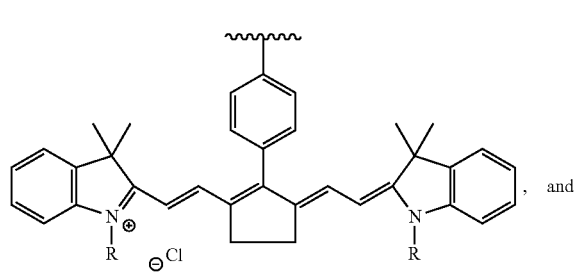

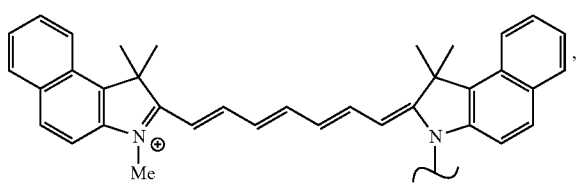

wherein each R is independently selected from H, $CH_3$, $C_2H_5$ and $C_3H_7$.

Linkers useful in the present invention include, but are not limited to, a bond, biotin-streptavidin linker, an azetidinone linker, and an amine-, azide-, alkyne-, carboxyl-, hydroxyl- group linker and combinations thereof.

The following preferred embodiments are provided solely for illustrative purposes and are not meant to limit the invention in any way.

Preferred Embodiments

In a preferred embodiment, the present invention is directed to a method of identifying a circulating prostate cancer cell comprising:

(i) contacting a blood or blood serum sample from a subject with a composition comprising a compound of the formula (V)

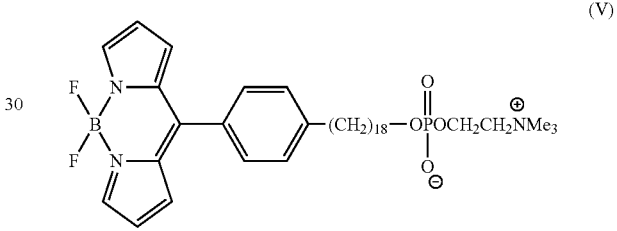

CLR1501 or formula (VI)

(VI)

CLR1502 and (ii) subjecting the blood or blood serum sample from the subject to fluorescent microscopy or flow cytometry.

In a preferred embodiment, the present invention is directed to a method of isolating a circulating prostate cancer cell comprising:

(i) contacting a blood or blood serum sample from a subject with a composition comprising a compound of the formula (V)

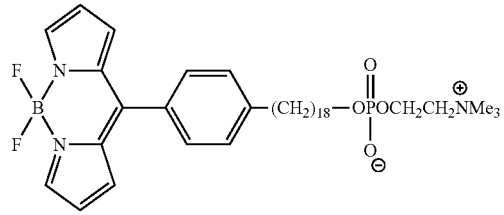

CLR1501 or formula (VI)

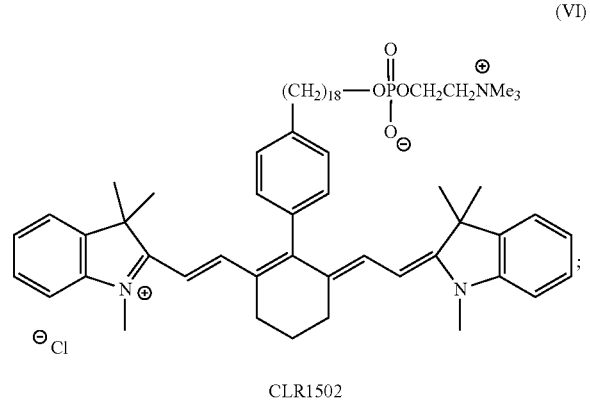

CLR1502 and (ii) subjecting the blood or blood serum sample from the subject to fluorescence activated cell sorting.

The following examples are provided solely for illustrative purposes and are not meant to limit the invention in any way.

EXAMPLES

Example 1-Synthesis of a PLE-Magnetic Bead Conjugate

First, both a PLE of formula I-IV and a magnetic bead as described herein, are each attached to its own functional group. The functional groups are then bound through click chemistry. As an example, a PLE of formula I of the present invention can be attached to an azide functional group and a magnetic bead can be attached to an alkyne functional group. The azide and alkyne functional groups can then be bound through click chemistry such as Copper-Catalzyed Azide-Alkyne Cycloaddition ("CuAAC".) In general, magnetic beads attached to a functional group are known as "functionalized magnetic beads" and are available from multiple sources such as Nanocs, Inc.

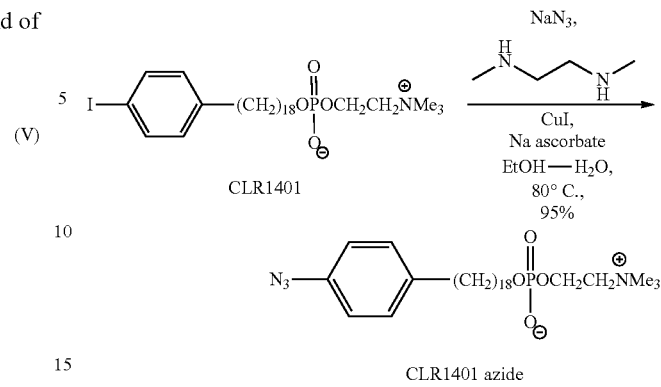

Synthesis of CLR1401 azide 18-(p-Iodophenyl)octadecyl phosphocholine (4.01 g, 6.3 mmol), sodium azide (818 mg, 12.6 mmol) and sodium ascorbate (140 mg, 0.71 mmol) were dissolved in the mixture of degassed ethanol (28 ml) and water (12 ml) in the reaction vessel. Copper (I) iodide (120 mg, 0.63 mmol) and N,N'-dimethyl-ethylenediamine (0.1 ml, 0.94 mmol) were added to the reaction mixture. Reaction vessel was tightly closed and the mixture was stirred at 80° C. for 45 min. Reaction mixture was cooled to the room temperature, water (60 ml) was added, and the mixture was stirred for 30 min open to the air. The mixture was transferred to the separatory funnel, chloroform (80 ml) and methanol (52 ml) were added, and extraction was performed by shaking. Chloroform layer was removed, and extraction was repeated (2×80 ml of chloroform). Combined chloroform extracts were washed with 0.01 N HCl, dried over $Na_2SO_4$, filtered and evaporated to dryness. Residue was dissolved in chloroform (4 ml) and acetone (170 ml) was slowly added with stirring. The mixture was stirred for 30 min and filtered. The product was rinsed on the filter with acetone, and dried under high vacuum to give 3.31 g (95%) of 18-(p-azidophenyl)octadecyl phosphocholine.

Binding of a PLE-Azide to an Alkyne Functionalized-Magnetic Bead

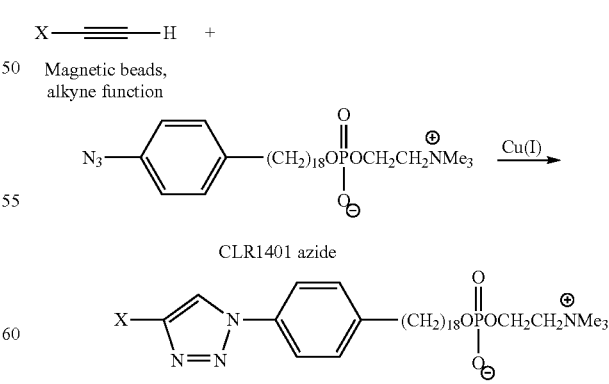

CLR1401 azide is bound to an alkyne functionalized magnetic bead through click chemistry. Above is an example of CuAAC. CuAAC is described in Himo F, et al., Copper (I)-catalyzed synthesis of azoles. DFT study predicts unprecedented reactivity and intermediates, *J Am Chem Soc*, 2005 Jan. 12, 127(1), 210-216, which is incorporated by reference in its entirety. Briefly, the alkyne functionalized magnetic bead and CLR1401 azide are mixed in a 1:1 ratio of water and tert-butyl alcohol in the presence of a copper oxide ("Cu(I)") catalyst for 6 to 12 hours. Optionally sodium ascorbate is added to the mixture. The final PLE-magnetic bead can then be isolated from the solution using simple filtration or extraction.

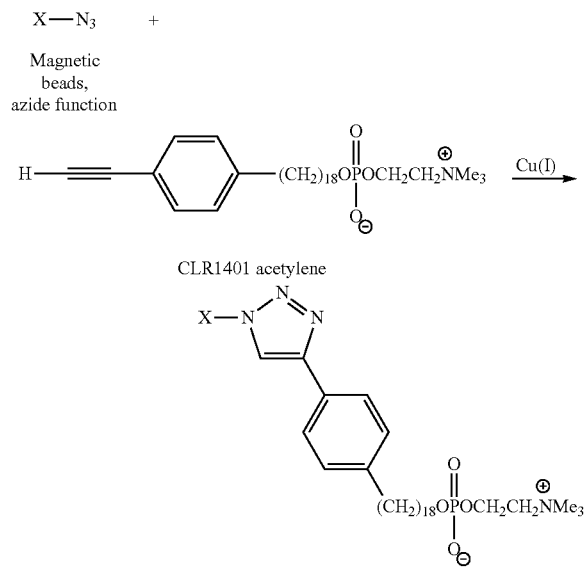

Binding of a PLE-Acetylene to an Azide Functionalized-Magnetic Bead

CLR1401 acetylene is bound to an azide functionalized magnetic bead through click chemistry. The same CuAAC reaction used for binding of CLR1401 azide to an alkyne functionalized magnetic bead can be used as described above.

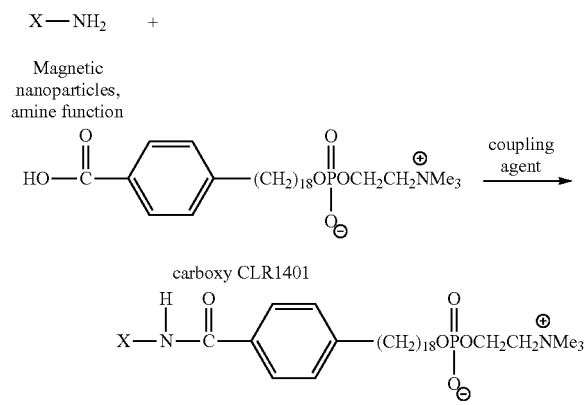

Binding of a Carboxy-PLE to an Amine Functionalized-Magnetic Nanoparticle

Carboxy CLR1401 is bound to an amine functionalized-magnetic nanoparticle through amide bonding. Amide bonding can be achieved with any coupling reagent suitable for formation of an amide bond, such as reagents used for peptide synthesis including, but not limited to, (2-(1H-benzotriazol-1-yl)-1,1,3,3-tetramethyluronium hexafluorophosphate) ("HBTU"), (1-[Bis(dimethylamino)methylene]-1H-1,2,3-triazolo[4,5-b]pyridinium 3-oxid hexafluorophosphate) ("HATU"), COMU® (COMU is available from Sigma Aldrich Co, LLC and is a registered trademark of Luxembourg Biotechnologies Ltd.) and propane phosphonic acid anhydride ("PPAA" or T3P®, T3P is available through and a registered trademark of Euticals SPA.)

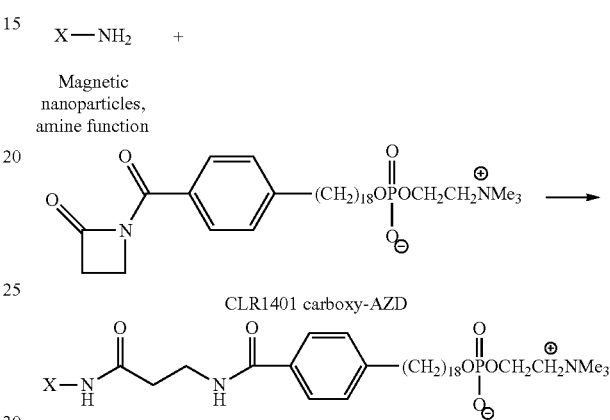

Binding of a PLE Carboxy-AZD to an Amine Functionalized-Magnetic Nanoparticle

Alternative to the amide bonding described above, amine-functionalized magnetic nanoparticles may be bound to a carboxy-PLE through an azetidinone ("AZD") linker. As an example, CLR1401 carboxy-AZD can be bound to an amine-functionalized magnetic nanoparticle via an AZD linker. AZD linkage is described in Roberts L R et al., Kappa agonist CovX-Bodies, *Bioorg Med Chem Lett,* 2012 Jun. 15, 22(12), 4173-4178 and Sato S et al., Chemically Programmed Antibodies AS HIV-1 Attachment Inhibitors, *ACS Med Chem Lett,* 2013 May 9, 4(5), 460-465.

Example 2—Identification and Enumeration of Circulating Tumor Cells of Lung, Thyroid, Breast, Cervical, Squamous Cell Carcinoma, and Colorectal Cancer Patients Using a Fluorescent PLE Analog Methods Whole blood was collected in either Cell Save® collection tubes or ethylenediaminetetraacetic acid ("EDTA") collection tubes from seven cancer patients with lung (patients 101 and 103), thyroid (patient 102), breast (patient 106), cervical (patient 104), squamous cell carcinoma (107), and colorectal (patient 108) cancer prior to (draw 1) and after (draw 2) therapy, when available. Mononuclear cells were isolated from the whole blood using a Ficoll-Paque density gradient. Cells from each patient were then incubated with an Fc blocker. The cells were then stained with fluorescently-tagged antibodies to CD45, CD14, CD34, EpCAM, and pan-Cytokeratin (CK), and a fluorescent PLE analog ("CLR1501") for 30 minutes. Cells were then analyzed by flow cytometry to indicate the number of cells from each whole blood sample that were positive and/or negative for a particular marker. According to the current definition, CTCs were identified as live cells that were CD45−, CD14−, CD34−, CK+, and EpCAM+ ("by definition"). Due to prior experience with CD14+ monocytes/macrophages (FIG. 1), CD14+ cells were removed from the analyses due to high uptake of CLR1501. CD34+ normal epithelial cells were also removed from the analyses. In comparison, the remaining CD45+ and CD34+ cells in the same patient will not take up CLR1501 to a large extent. The results from this analysis is explained below and summarized in Tables 1 and 2.

The first row of Tables 1 and 2 depicts the number of cells from each patient's blood draw that fulfilled the definition of a CTC: CD45−, CD14−, CD34−, CK+, and EpCAM+, and contained a nucleus. The second row depicts the number of cells from each patient's blood draw that were CD45−, CD14−, CD34−, CK+, and contained a nucleus. The third row depicts the number of cells from each patient's blood draw that were CLR 1501+, CD45−, CD14−, CD34−, CK+, and contained a nucleus. The fourth row depicts the number of cells from each patient's blood draw that were CD45−, CD14−, CD34−, and EpCAM+ and contained a nucleus. The fifth row depicts the number of cells from each patient's blood draw that were CLR 1501+, CD45−, CD14−, CD34−, and EpCAM+ and contained a nucleus. The sixth row depicts the number of cells from each patient's blood draw that were CLR 1501+, CD45−, CD14−, CD34−, CK−, and EpCAM−, and contained a nucleus.

TABLE 1

Identification and Enumeration of Circulating Tumor Cells in Blood Samples of Patients with Varying Cancer Types Collected in Cell Save ® Collection Tubes

| Cell Save ® (number) | Lung Cancer 101 (1) | Lung Cancer 101 (2) | Thyroid Cancer 102 (1) | Thyroid Cancer 102 (2) | Lung Cancer 103 | Cervical Cancer 104 (1) |
|---|---|---|---|---|---|---|
| CTC's (by definition) | 0 | 10 | 29,980 | 22,246 | 6,380 | 944 |
| CK+ | 4.7M | 10 | 1.0M | 3.5M | 3.3M | 6.8M |
| CK+/CLR 1501+ | 4.7M | 10 | 1.0M | 3.3M | 3.3M | 6.8M |
| EpCAM+ | 20 | 41 | 38,594 | 24,674 | 10,610 | 1,087 |
| EpCAM+/CLR 1501+ | 20 | 31 | 37,355 | 24,919 | 11,139 | 998 |
| CK−/EpCAM−/CLR1501+ | 1.4M | 121,696 | 6.7M | 7.9M | 5.3M | 1.3M |

| Cell Save ® (number) | Cervical Cancer 104 (2) | Breast Cancer 106 | Carcinoma 107 | Colorectal Cancer 108 (1) | Colorectal Cancer 108 (2) |
|---|---|---|---|---|---|
| CTC's (by definition) | 26 | 30 | 1,034 | 5 | 30 |
| CK+ | 789 | 60 | 54,661 | 5 | 15,423 |
| CK+/CLR 1501+ | 789 | 60 | 54,391 | 5 | 15,418 |
| EpCAM+ | 1069 | 105 | 6,968 | 40 | 222 |
| EpCAM+/CLR 1501+ | 942 | 75 | 6,686 | 15 | 109 |
| CK−/EpCAM−/CLR1501+ | 36.4M | 278 | 611,622 | 1,062 | 1.1M |

M denotes million

M Denotes Million

TABLE 2

Identification and Enumeration of Circulating Tumor Cells in Blood Samples of Patients with Varying Cancer Types Collected in EDTA Collection Tubes

| | Lung Cancer | Lung Cancer | Thyroid Cancer | Thyroid Cancer | Lung Cancer |
|---|---|---|---|---|---|
| EDTA (number) | 101 (1) | 101 (2) | 102 (1) | 102 (2) | 103 |
| CTC's (by definition) | 26 | 0 | 730 | 8,808 | 192 |
| CK+ | 1.8M | 0 | 46,155 | 16,797 | 13,290 |
| CK+/CLR 1501+ | 1.8M | 0 | 46,132 | 16,755 | 13,012 |
| EpCAM+ | 178 | 0 | 2,353 | 10,236 | 1,517 |
| EpCAM+/CLR 1501+ | 153 | 0 | 2,720 | 10,375 | 1,896 |
| CK−/EpCAM−/CLR1501+ | 1.8M | 30,222 | 1.5M | 10.9M | 2.5M |

| | Cervical Cancer | Breast Cancer | Carcinoma | Colorectal Cancer | Colorectal Cancer |
|---|---|---|---|---|---|
| EDTA (number) | 104 | 106 | 107 | 108 (1) | 108 (2) |
| CTC's (by definition) | 22,965 | 12 | 1,896 | 0 | 76 |
| CK+ | 9.6M | 98 | 13,805 | 76 | 968 |
| CK+/CLR 1501+ | 9.6M | 86 | 13,788 | 76 | 917 |
| EpCAM+ | 24,722 | 17 | 8,088 | 662 | 433 |
| EpCAM+/CLR 1501+ | 23,493 | 17 | 9,469 | 382 | 229 |
| CK−/EpCAM−/CLR1501+ | 4.0M | 19,585 | 147,641 | 29,584 | 753,387 |

M denotes million

Results

All seven samples contained detectable CTCs (by definition) that showed positive uptake of CLR1501 (compare row 1 to rows 3, 5 and 6 in Tables 1 and 2). A representative flow cytometry image depicting high uptake of CLR1501 in CD14+ cells of blood samples from patient 8 is shown in FIG. 1. In FIG. 1, upper left quadrant indicates CD14−/CLR1501+ cells, upper right indicates CD14+/CLR1501+, bottom right indicates CD14+/CLR1501−, and bottom left indicates CD14−/CLR1501−. In panel A, cells negative for CD45 and CD34 (i.e. possible circulating tumor cells) isolated from blood drawn from patient 108 is shown stained with all markers, except Brilliant Violet 785™ CD14. Cells positive for CD14 labeled are shown on the x-axis and cells positive for CLR1501 on the y-axis. Panel A was used as a control to set the gates for Brilliant Violet 785™ CD14 positive cells. In panel B, cells negative for CD45 and CD34 isolated from blood drawn from patient 108 is shown stained with all markers, including Brilliant Violet 785™ CD14. As shown, 99.7% of cells positive for CD14+ are also positive for CLR1501. Compare FIG. 1, panel B to panel A.

Further, CLR 1501 was able to identify ~99-100% of CK+ cells (compare row 2 to row 3 of Table 1 or 2) and ~35-100% of EpCAM+ cells (compare rows 4 or row 5 of Table 1 or 2), in all cancer types irrespective of which blood collection tube was utilized. Surprisingly, there were a large number of cells that were CLR 1501+, but CK-, EpCAM-, CD45-, CD14-, CD34-, and contained a nucleus (row 6, Tables 1-2). Cells indicated in row 6 of Tables 1 and 2 are not blood cell types but may be other tumor cells which may have decreased or no expression of EpCAM and CK. Many cancers are reported to either express alternative tumor markers, have heterogeneous expression of EpCAM and/or CK, or may be undergoing epithelial-mesenchymal transition (EMT) and thus, losing expression of epithelial markers. Yu 2013, Eichelberg 2013 and Spizzo 2011. Thus, CLR1501 is capable of identifying circulating tumor cells that would otherwise go undetected in current single and multi-marker assays.

Patients 101, 102, 104 and 108 had blood draws taken prior to and after therapy (Draw 1 and 2, respectively). Patient 101 had a very good partial response to therapy; however, from Draw 1 to 2, this patient's CTC count by definition increased from 0 to 10, indicating progression of the cancer (Table 1). If only CK was utilized as a marker of tumor cells, Patient 101's tumor cell count decreased from 4.7 million to 10 (Table 1, compare Draw 1 to Draw 2). If only EpCAM was utilized as a marker of tumor cells, Patient 101's tumor cell count increased from 20 to 41 (Table 1, compare Draw 1 to Draw 2). However, Patient 101's total tumor cell count (both CK+ and EpCAM+ numbers) decreased from Draw 1 to Draw 2, indicating that separate markers may be a more accurate measurement of clinical response and that Patient 101's cancer cells portray heterogeneous expression of CK and EpCAM. Furthermore, Patient 101's count of all CLR 1501+ cells decreased dramatically from Draw 1 to 2. This trend is also seen in the EDTA blood collection tubes for Patient 101 (Table 2.) Thus, CLR 1501 alone may be a more accurate measurement of clinical response than current assays, negating the need for identification of both EpCAM and CK.

Overall, the fluorescent PLE analog CLR1501 was successfully used to identify CTCs from lung, thyroid, breast, cervical, squamous cell carcinoma, and colorectal cancer patients.

What is claimed is:

1. A method of isolating tumor cells comprising the steps of:
    (i) contacting a blood or blood serum sample from a subject having one or more circulating tumor cells (CTCs) with a compound of formula (I),

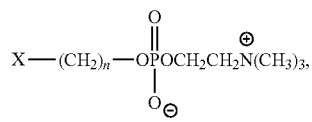

formula (II)

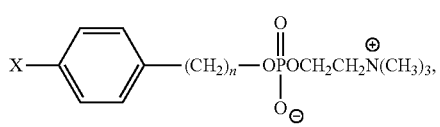

formula (IV)

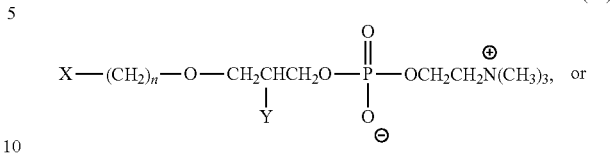

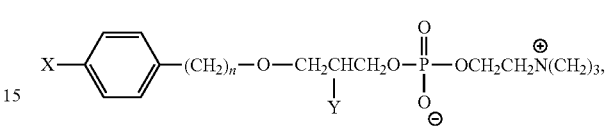

wherein:

n is an integer from 16 to 30;

Y is selected from the group consisting of —H, —OH, —OR, —C(O)OH, and —OC(O)R, wherein R is an alkyl; and X is a luminescent molecule;

(ii) subjecting the blood or blood serum sample to flow cytometry; and
   (iii) isolating the one or more CTCs following (ii), wherein the one or more CTCs are selected from the group consisting of a breast cancer cell, a lung cancer cell, a thyroid cancer cell, a cervical cancer cell, a squamous cell, a carcinoma cell, a prostate cancer cell, a pancreas cancer, a colorectal cancer cell, and a cancer stem cell.

2. The method of claim 1, wherein the luminescent molecule is a fluorophore.

3. The method of claim 2 wherein the fluorophore is selected from the group consisting of

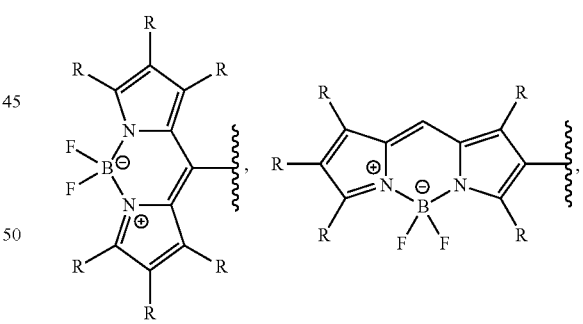

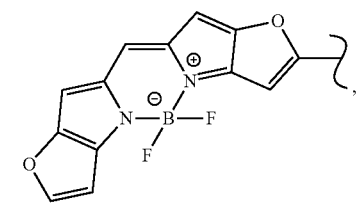

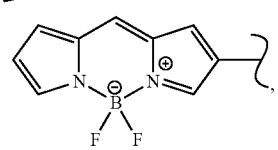

-continued

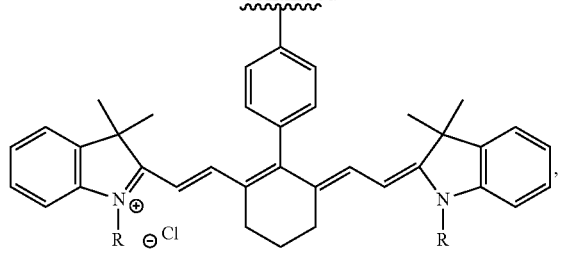

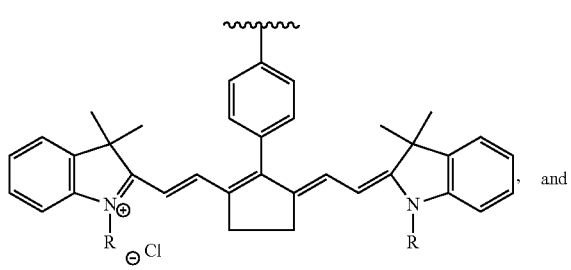

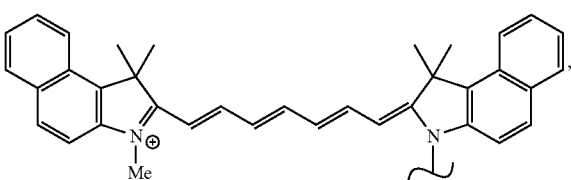

wherein each R of the fluorophore is independently H, CH₃, C₂H₅, or C₃H₇.

4. The method of claim 3 wherein the compound is a compound of formula (II) and the fluorophore is selected from the group consisting of

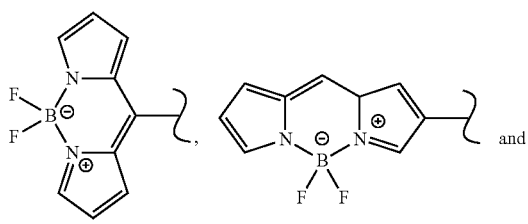

-continued

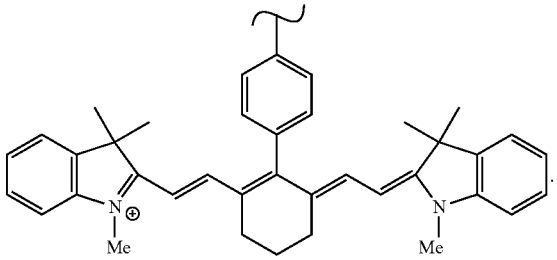

5. The method of claim 1, wherein the flow cytometry comprises fluorescence activated cell sorting.

6. The method of claim 1, further comprising utilizing the one or more isolated CTCs in a technology selected from the group consisting of protein isolation, RNA isolation, DNA isolation, gene translocation analysis, gene amplification analysis, and fluorescent in-situ hybridization.

7. The method of claim 1, wherein the one or more circulating tumor cells are prostate cancer cells.

8. The method of claim 7, wherein the compound is a compound of formula (V),

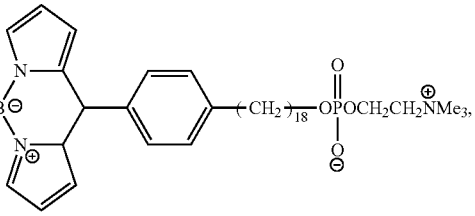

or a compound of formula (VI), (VI)

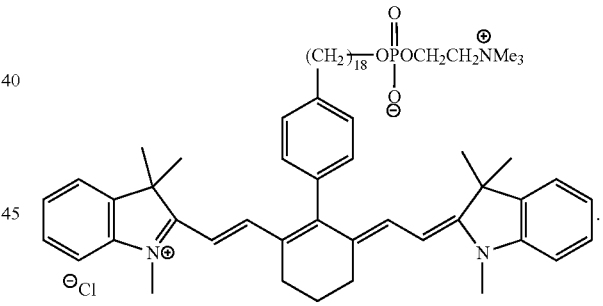

* * * * *